United States Patent [19]
Colling

[11] Patent Number: 5,416,469
[45] Date of Patent: May 16, 1995

[54] METHOD FOR PREDICTION OF TIMES OF VOIDING UTILIZING TEMPERATURE MEASUREMENTS

[76] Inventor: Joyce C. Colling, 10185 SW. View Ter., Tigard, Oreg. 97224

[21] Appl. No.: 287,480

[22] Filed: Aug. 8, 1994

Related U.S. Application Data

[60] Continuation-in-part of Ser. No. 145,002, Oct. 29, 1993, abandoned, which is a division of Ser. No. 13,125, Feb. 3, 1993, Pat. No. 5,258,743, which is a continuation of Ser. No. 813,213, Dec. 23, 1991, abandoned.

[51] Int. Cl.⁶ .................................... G08B 21/00
[52] U.S. Cl. ......................... 340/573; 128/885; 128/886; 340/584; 340/604; 364/413.02
[58] Field of Search ............... 340/573, 604, 584, 585; 364/413.02, 415.04; 128/886, 885, DIG. 25

[56] References Cited

U.S. PATENT DOCUMENTS

| | | | |
|---|---|---|---|
| 3,460,123 | 8/1969 | Bass | 340/573 |
| 4,205,671 | 6/1980 | Lassen | 340/604 |
| 4,271,406 | 6/1981 | Wilson | 340/604 |
| 4,356,479 | 10/1982 | Wilson | 340/604 |
| 4,539,559 | 9/1985 | Kelly et al. | 340/573 |
| 4,653,491 | 3/1987 | Okada et al. | 128/886 |
| 4,738,260 | 4/1988 | Brown | 128/886 |
| 4,800,370 | 1/1989 | Vetecnik | 340/573 |
| 4,975,842 | 12/1990 | Darrow et al. | 364/413.02 |
| 4,977,906 | 12/1990 | Di Scipio | 340/604 |
| 5,082,002 | 1/1992 | Silverman et al. | 364/413.02 |

Primary Examiner—Glen Swann, III
Attorney, Agent, or Firm—Stoel Rives Boley Jones & Grey

[57] ABSTRACT

A temperature sensor (10), which is connected to a sampling/recording meter (14), is imbedded in a diaper (22). The meter measures and records the temperature of the sensor at time intervals of, for example, one minute over a predetermined period of, for example, three days. The temperature and time data are then loaded from the meter to a computer (30), which causes a printer (40) to plot temperature versus time data in graphical format, and numerical format. Voiding events are identified. Thereafter, at a short time before the person will void, the person can voluntarily use a toilet or bed pan either alone or with the assistance of care giver. This voluntary voiding is an example of intervention. The meter includes an event button (44) that allows the recording and later printing of a symbol representing a specific event and the time the event occurred. The symbols may be used in identifying voiding events.

13 Claims, 3 Drawing Sheets

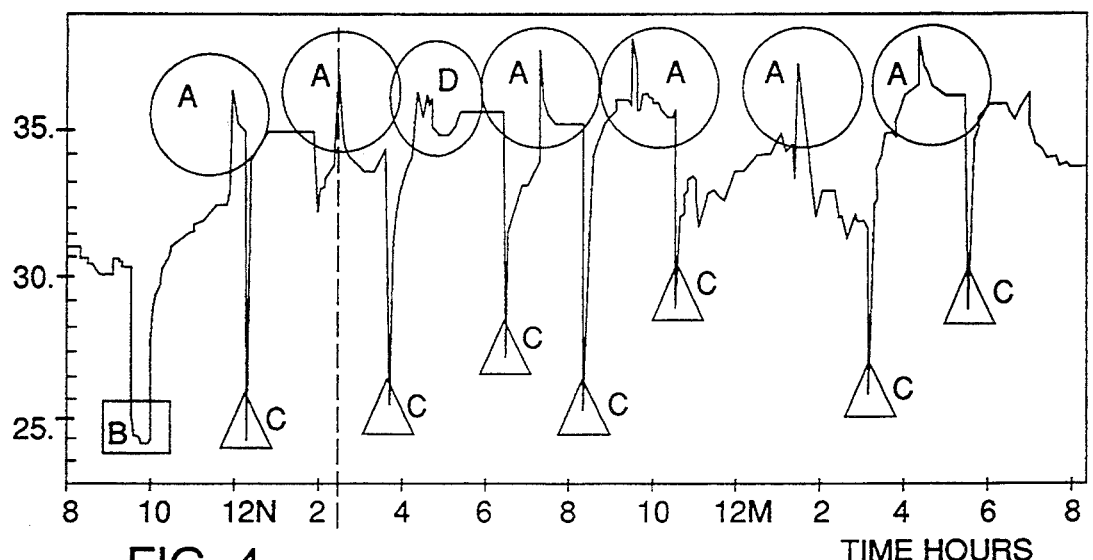
FIG. 4
FIG. 5
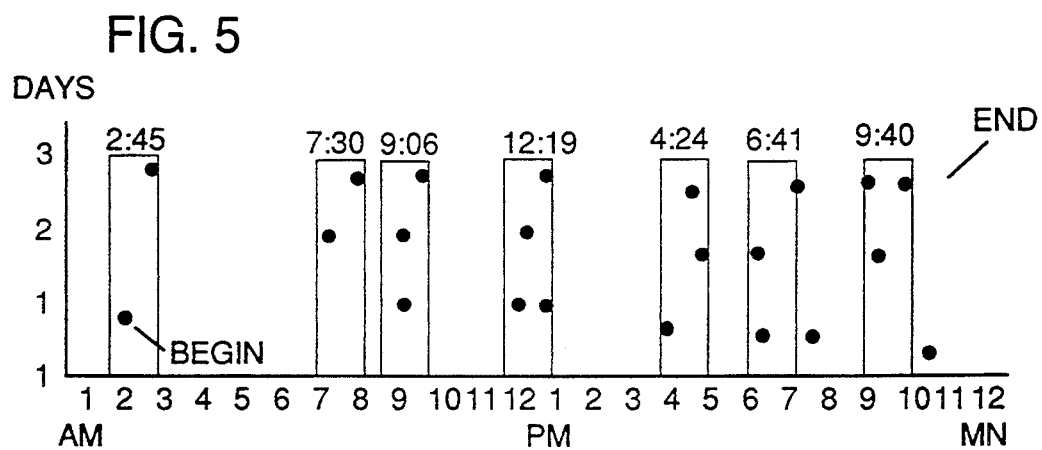
FIG. 6
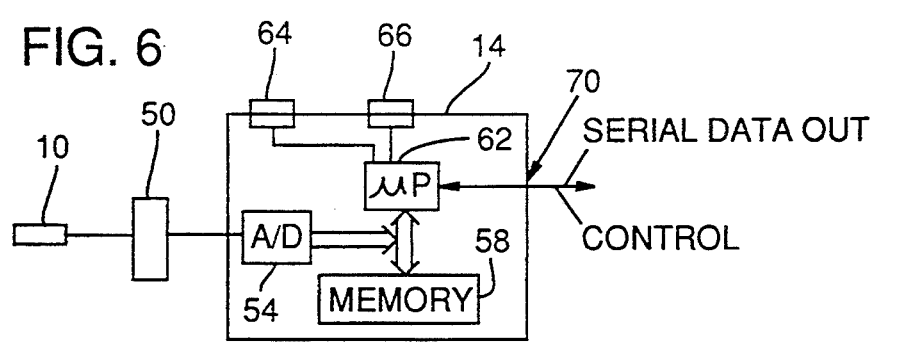

METHOD FOR PREDICTION OF TIMES OF VOIDING UTILIZING TEMPERATURE MEASUREMENTS

STATEMENT OF GOVERNMENT INTEREST

This invention was made with government support under NIH Grant NR-01554, "Patterned Urge Response Toileting for Incontinence" (Urinary Incontinence Monitor), ID# OHSU 90 D# 171, awarded by the National Institute of Health. The Government has certain rights in the invention.

This is a continuation in part of application Ser. No. 08/145,002, filed Oct. 29, 1993, now abandoned, which is a division of application Ser. No. 08/013,125, filed Feb. 3, 1993, now U.S. Pat. No. 5,258.743, which is a continuation of application Ser. No. 07/813,213, filed Dec. 23, 1991, now abandoned.

TECHNICAL FIELD

The present Invention relates to a system and method for accurately predicting approximate times an incontinent person without intervention would void in the future.

BACKGROUND OF THE INVENTION

Incontinent persons often urinate or void in a diaper or clothing rather than in a toilet causing significant discomfort and distress to the person. In addition, there is considerable expense to nursing homes or changing the diaper or clothing as well as providing these disposable supplies. The costs for such supplies and services has been estimated at 3 billion dollars per year.

Various devices have been invented to indicate when a person voids so that the person's diaper or clothing may be changed. For example, U.S. Pat. No. 3,460,123 of Bass, U.S. Pat. No. 4,271,406 or Wilson, U.S. Pat. No. 4,556,479 of Wilson, U.S. Pat. No. 4,539 559 of Kelly et al., U.S. Pat. No. 4,738,260 of Brown describe systems that set off an alarm after a person being monitored voids. These systems include circuits that are closed through urine. See U.S. Pat. No 3,460,123 (conductor screens 30 and 32); U.S. Pat. No. 4,271,406 (moisture sensing electrodes 30); U.S. Pat. No. 4,356,479 (magnetic sensing electrodes 30); U.S. Pat. No. 4,539,559 (absorbent pad 2); U.S. Pat. No. 4,738,260 (urine sensing pad 12 and sheath 102: col. 3, lines 6-7, col. 5, lines 6-8).

U.S. Pat. No. 4,800,370 of Vetecnik describes a wetness detection system that detects dampness in a diaper or other clothing and triggers an alarm when a conductive bath between conductor wires 224 is closed. The Vetecnik patent also describes an additional feature that provides a reading of the patient's temperature or "body heat." See col. 3, lines 63-65 and col. 5, lines 27-30. As shown in FIG. 3, detector/transmitter 4 is attached between the skin of a person 308 and a diaper 300 by a spring clip 204. The temperature of the skin is measured by means of a thermistor 412 (shown in FIG. 4) located inside housing 200 of detector/transmitter 4 shown in FIG. 2) The temperature of the urine is not measured because the urine is located away from housing 200. Note that elongated conductor strip 216 (shown in FIGS. 2 and 4) travels down the diaper toward the location of the urine.

U.S. Pat. No. 4,653,491 of Okada et al. describes a system that measures the amount of wetness in a diaper by measuring capacitance. When the capacitance exceeds a limit, an alarm is set off.

A problem with the systems of each of above-cited patents is that they determine only the occurrence of urination after it has happened. The systems do not help the incontinent person to avoid the situation.

U.S. Pat. No. 4,977,906 of DiScipio describes a system including sensors 12 and 13, which are placed in an undergarment, such as a diaper. During an enuresis incidence, moisture is absorbed in the undergarment. When the undergarment is sufficiently wet, the open circuit across sensors 12 and 13 is completed resulting in an alarm being set off. The DiScipio patent states it is possible to monitor occurrences of urine discharge and determine when future occurrences are likely. The information can be used to forewarn the patient of the likelihood of a enuresis incident.

A problem with the system of the DiScipio patent is that as long as the diaper remains wet, the open circuit across sensors 12 and 13 remains completed. The system cannot recognize the situation when a person voids twice before the diaper is dry. Therefore, the predictive value of the system is limited.

There is, therefore, a need for a system that can detect urination even though the diaper of the person is wet.

SUMMARY OF THE INVENTION

It is, therefore, an object of the invention to provide a method and system for detecting voiding in an undergarment whether or not the undergarment is still wet from a previous voiding.

Another object of the invention is to provide a method and system for predicting the times of future voiding by a person by periodically sampling the temperature obtained by a sensor which is over a long period of time placed near the urethral opening of the person.

Still another object of the invention is to provide a system with an event button that when activated records a symbol that can later be used to indicate times a person voided and whether the voiding occurred in the undergarment or a toilet.

The present invention relates to a system and method for accurately predicting approximate times an incontinent person without intervention would void in the future. A temperature sensor, which is connected to a sampling/recording meter, is imbedded in a diaper. The meter measures and records and stores the temperature of the sensor at time intervals of, for example, one minute over a predetermined period of, for example, three days. The temperature and time data are then loaded from the meter to a computer, which causes a printer to plot temperature versus time data in graphical format. A pattern of voiding events are identified and a voiding schedule is constructed for the person based on his usual voiding times. Thereafter, at a short time before the person will void, the person can voluntarily use a toilet or bed pan either alone or with the assistance of care giver. This voluntary voiding is an example of intervention. The meter includes an event button that allows the recording and later printing of a symbol representing a specific event and the time the event occurred. The symbols may be used in identifying voiding events.

BRIEF DESCRIPTION OF THE DRAWINGS

FIG. 4 shows exemplary temperature vs. time data, which is printed by the computer.

FIG. 5 shows composite analyzed temperature vs. time data.

FIG. 6 shows details of one example of the sampling/recording meter.

DETAILED DESCRIPTION OF PREFERRED EMBODIMENT

People often urinate at very near the same times every day. The times at which such a person urinates may be predicted by use of the present invention. The person may voluntarily void in a toilet or bed pan shortly before the predicted times of voiding. A care giver may assist the person in voiding in a toilet or bed pan. In this regard, it is expected that the invention will be used primarily by incontinent people. However, the invention also may be used by those people who are continent but that through some physical problem have difficulty in urinating in a toilet or bed pan without help. Many, but not all, of the persons using the invention will be older persons in nursing homes or at home who are receiving assistance from care givers.

Figure 1:
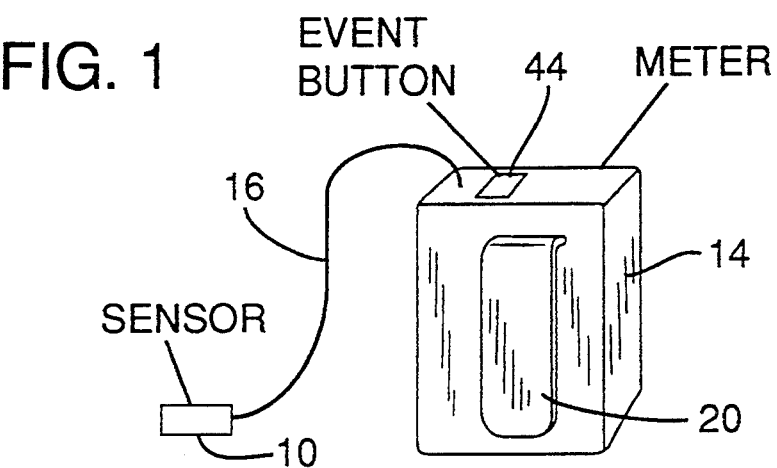
FIG. 1 shows the temperature sensor and sampling/recording meter of the present invention.
Figure 2:
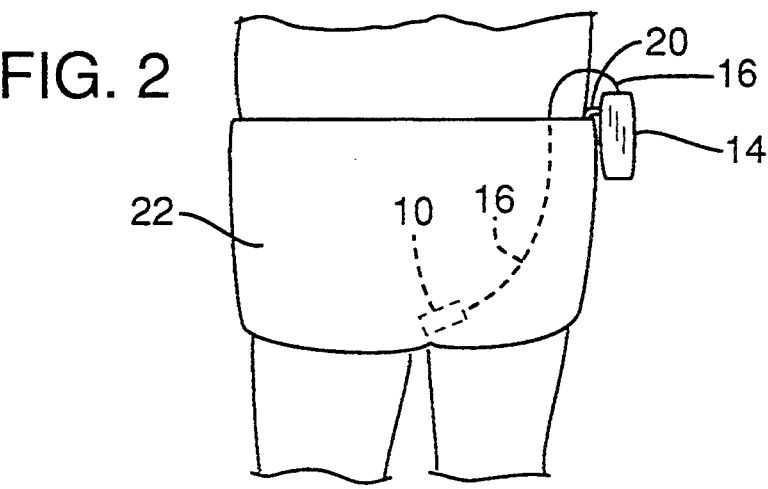
FIG. 2 shows placement of the temperature sensor and sampling/recording meter in operation.

Referring to FIG. 1, the present invention includes a temperature sensor 10 that is connected to a sampling/recording meter 14 via conductors 16. Referring to FIG. 2, in operation, meter 14 is attached by clip 20 to an undergarment, such as diaper 22. As used herein, "undergarment" means a diaper, underpants, pad, or other article of clothing suitable to be worn around the waist and legs of a person. The undergarment includes a region that is near the urethral opening of the person when the undergarment is worn. Sensor 10 is placed near the region such that sensor 10 will be in direct contact with or close to discharged urine. Sensor 10, shown in dashed lines, is embedded in or otherwise secured to or placed next to diaper 22.

Meter 14 records the temperature of sensor 10 at time intervals of, for example, one minute over a predetermined period of, for example, three days. After temperature samples have been taken for the predetermined period, the temperature and time data are down loaded from meter 14 to a computer 30, shown in FIG. 3. Under the command of computer 30, printer 40 plots the temperature versus time data sampled and recorded by meter 14. The plotted data is analyzed to determine at what times of day the person regularly voids. Thereafter, at a short time before the person will void, the person can voluntarily use a toilet either alone or with the assistance of care giver.

The operation of sensor 10 and the sampling and recording feature of meter 14 is illustrated by FIG. 4, which shows exemplary plotted temperature vs. time data plotted by printer 40. The temperature vs. time data was sampled and recorded by meter 14 over a twenty-four hour period. The temperature shown in FIG. 4 is the temperature sensed by sensor 10 and measured by meter 14. In FIG. 4, "A" indicates a voiding event; "B" indicates diaper 22 was removed for a morning bath; "C" indicates diaper 22 was removed for changing; and "D" indicates a bowel movement.

At 8:00 AM, when the samples begin, diaper 14 is dry and the temperature sensed by sensor 10 is about 31 degrees Celsius (°C.). Diaper 22 remains dry and the temperature remains at around 31° C. until about 9:30 AM, when diaper 22 is removed during the person's bath. When diaper 22 is removed, sensor 10 senses and meter 14 measures ambient air temperature. At slightly before 10:00 AM, the same or a different diaper is put back on the person and meter 14 makes additional temperature measurements.

From about 10:00 AM to about 11:45 AM, the measured temperature increases from about 30° C. to 32.5° C. The measured temperature can change by a relatively large amount even though there is no voiding because of changes of body temperature, heat caused by movement of diaper 22 against the skin the person, and changes in the position of sensor 10 with respect to the skin of the person.

At about 11:50 AM, the temperature sensed by sensor 10 rapidly increases to about 36° C. and then quickly decreases over approximately the next fifteen minutes to about 35° C. The plotted samples from about 11:50 AM to 12:05 PM are circled and marked with an "A." Temperature versus time samples having this type of rapid rise and slower decrease in temperatures typically indicate a voiding episode. Shortly after about 12:05 PM, when diaper 22 is removed, sensor 10 senses ambient air temperature. The time during which the diaper is removed is denoted by a triangle and the letter "C."

After diaper 22 is put back on the person the measured temperature shoots back up to about 35° C. and remains there from about 12:30 PM to 2:00 PM. Even though the temperature is relatively high from about 12:30 to 2:00 PM, the flatness of the temperature data indicates the lack of voiding. It is likely that sensor 10 was close to the skin of the person from about 12:30 PM to 2:00 PM and, therefore, picked up a relatively large amount of body temperature. 35° C. is close to the body temperature of 98.6° F. By contrast, from about 8:00 AM to 9:30 AM, sensor 10 was probably positioned farther from the body and, therefore, measured a lower temperature.

At about 2:30 PM, there is another voiding episode which is indicated by a sharp temperature peak and subsequent declining temperature. A vertical line is shown at about 2:30 PM, which is initiated by activation of event button 44, shown in FIG. 1 and described below. After the diaper is changed at about 3:40 PM, the measured temperature steadily increases until there are two small peaks at about 36° C. from about 4:15 to 4:30 PM. The peaks represent a bowel movement, and are uncharacteristic of urination. The bowel movement is indicated by a circled letter "D." At about 6:15 PM, the diaper is changed.

There are additional times of voidings, which are circled and marked with an "A" at about 7:15 PM, 9:45 PM, 1:45 AM, and 4:30 AM.

The following is a method for determining when voiding events occurred by observing the temperature vs. time data plotted on FIG. 4. First, voiding events are characterized by sharp spikes of, for example, as much as 2 or 3 degrees in temperature. The sharp spikes are followed by a gradual decline in temperature toward the temperature prior to the voiding event. However, movement by the person wearing the diaper can change the temperature measured by sensor 10.

The method of prediction can be performed by inspection and hand plotted. Alternatively, or in addition, the times could be predicted by computer 30 under an algorithm that follows the procedure described above.

In addition to the rules disclosed above, notes may be taken by the nurse or person under test of each time the diaper is changed when there has been voiding and when there has not been voiding. Also, the person under test can note each time they urinate. In this respect, an event button 44 on meter 14 may be activated, which causes a particular symbol to be recorded in meter 14. The symbol may be vertical lines that are printed on the graph of FIG. 4. For example, a single vertical line is shown on FIG. 4 at about 2:30 PM. When event button 44 is activated once at a given time, one vertical line should are printed for that time. When event button 44 is activated twice in a short time, two vertical lines are printed for that time. Alternatively, meter 14 could include a different event button for each type of event.

Event button 44 may be used to indicate various events. For example, activating event button 44 once can be used to indicate voiding in diaper 22. Activating event button 44 twice within a very short time period can indicate voiding in a toilet or bed pan. Activating event button 44 three times can indicate a care giver removed a diaper that did not contain urine or a stool. Activating event button 44 four times can indicate a bowel movement. Of course, The vertical line(s) produced in response to activation of event button 44 are only helps in deciding whether a voiding event as occurred. The person under test or the care giver can forget to or otherwise fail to activate event button 44 at the appropriate time.

The accuracy of the prediction of voiding events may be increased by compiling data similar to that in FIG. 4 over several, for example, three days. FIG. 5 shows such a compilation. Referring to FIG. 5, black dots show the time of voiding for each of three days. The times of voiding in day 1 are shown as dots beneath the dots representing times of voiding in day 2, which in turn are beneath the dots representing times of voiding in day 3. Rectangles having a width corresponding to about one hour are drawn around clusters of dots. The placement of the rectangles is not an exact science but, as can be seen in the case of FIG. 5, the choice for placement of the rectangles is reasonably clear. The numbers on the top of the rectangles are the mean times of the times represented by the dots in the rectangles.

Predicting the time of voiding based on the mean time or any other such time is a prediction of an approximate time of voiding. Nevertheless, the prediction under the method of the present invention can be quite accurate in the cases of many people. The time of voiding may be thought of as a range rather than an approximate time, where the size of the range is a function of the accuracy of the approximate time. For example, about 85% of persons without voluntary control who were tested consistently voided within 30 minutes of mean time.

The time at which the person should voluntarily void with or without the help of others may be calculated under several methodologies. For example, a preferred time to voluntarily void is sometime between one-half hour before the mean time and the mean time of a cluster of voiding times within a rectangle, with the time preferably being closer to one-half hour before. Under other methods, the time to void is at the time of the beginning of the rectangle or a predetermined amount of time, e.g., 10 minutes, before the first voiding of a cluster of voidings. Voluntary voiding is an example of intervention. Another example of intervention is a significant change in the amount or time of intake of food, liquids, or drugs, or significant change in activity.

Initial study suggests that voluntary voiding does not change the time of future voiding. In the case of some persons, however, voluntary voiding may alter times of consumption of fluids and voiding enough to cause the predicted times to no longer be accurate. In that case, the procedure of the invention could be repeated.

An example of meter 14 is the Rustrak Ranger manufactured by Gulton Industries, Inc. of East Greenwich, R.I. The Rustrak Ranger was designed to sample temperature changes in industry where remote temperature monitoring is desirable. For example, the Rustrak Ranger has been used in monitoring the refrigeration temperature of perishables during transport via truck or train.

Referring to FIG. 6, a block diagram of the Rustrak Ranger is shown with sensor 10 connected to meter 14 through signal conditioning pod 50, which is also sold by Gulton Industries. Pod 50 includes four channels that may receive signals from sensors that measure and convert phenomena such as temperature, pressure, flow, voltage, current, etc., into analog signals representing the phenomena. For the present invention, only temperature is measured. Pod 50 converts the signal from sensor 10 into a standard signal level (zero to 2 volts, full scale) suitable for input to meter 14. Of course, meter 14 could be designed to accept signals directly from sensor 10 without pod 50.

Meter 14 includes analog to digital (A-to-D) converter 54 that receives data from pod 50. Data from A-to-D converter 54 is stored in memory 58 under the control of microprocessor 62. Select button 64 and enter button 66 control microprocessor 62. Enter button 66 is an example of event button 44.

Figure 3:
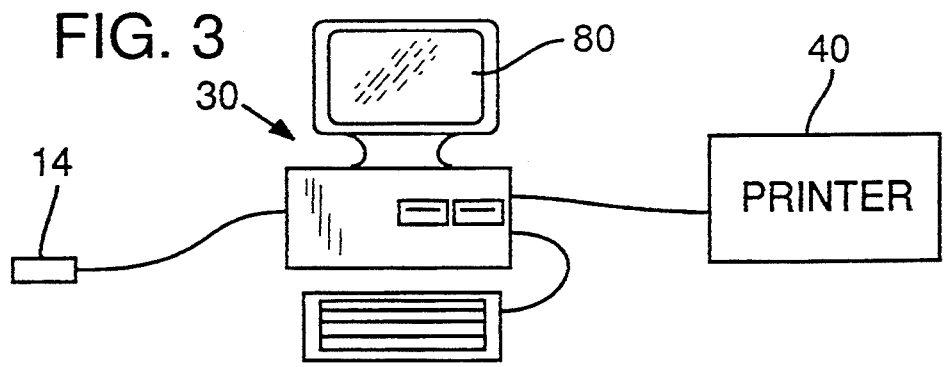
FIG. 3 shows the sampling/recording meter down loading information to a computer, and a printer for printing information from the computer.

The Rustrak Ranger is designed to be compatible with IBM PC computers. Referring to FIGS. 3 and 6, temperature data is loaded from microprocessor 62 to computer 30 through serial data output 70. Output 70 is connected to the RS-232 port of computer 30. The Rustrak Ranger is designed to be used with software called Pronto which is available from Gulton Industries, the manufacturer of the Rustrak Ranger. Pronto controls data transfer from output 70 to computer 30.

Pronto allows presentations of the temperature vs. time data in a variety of formats. For example, the temperature vs. time data may be displayed on monitor 80 of computer 30 or printed by printer 40, which may be an Epson printer. The data may be printed in graphical format as in FIG. 4 or as numerical values arranged in six columns. Column 1 includes the date, minute, and second the temperature sample was taken (e.g., 12:11:05:30); column 2 lists the temperature when the sample was taken (e.g., 35.34); column 3 lists the average between the current and previous temperature; column 4 lists the maximum temperature during the minute indicated in column 1; column 5 lists the minimum temperature during the minute indicated in column 1; and column 6 indicates whether any "events" were noted (i.e., whether event button 44 was pushed one or more times).

In the preferred embodiment, the time vs. temperature data of FIG. 4, which is plotted by printer 40, is generated only from the time data of column 1 and the temperature data of column 2; not from the data in columns 3, 4, and 5. A vertical line is preferably printed on the temperature vs. time graph of FIG. 4 for each time in which there is event data in column 6.

In the present invention, the temperatures measured by sensor 10 are typically within the range of roughly 18° to 45° C. The Rustrak Ranger is designed to be used with sensors 10 that measure temperature over a much wider range. For example, sensor 10 may be a thermistor with a temperature range of −40° to +110° C., in which case, pod 50 should be of the POD-03 type, as supplied by Gulton Industries. The Rustrak Ranger (i.e., meter 14) is adjustable for different temperature ranges and should be set appropriately for the range of the present invention. An example of the thermistor is 400 series temperature sensor, #081-440004-NA-FP-72-ST, marketed by Yellow Springs Instrument Co. of Yellow Springs, Ohio. Alternatively, sensor 12 may be a thermocouple (type J) with a temperature range of 0° to 400° C., in which case, pod 50 should be of the POD-06 type.

Another example of meter 14 is the Vitalog PMS-8 manufactured by Vitalog Corporation, which might be no longer in business. The PMS-8, which is relatively expensive, was designed to make measurements of physiological data.

Alternatively, rather than use a commercially constructed meter such as the Rustrak Ranger or PMS-8, meter 14 could be especially designed to perform the functions of the present invention. Likewise, the functions performed by Pronto could easily be performed by especially written software. The meter would ideally be no larger than about 2"×3"×1" (5.1 cm×7.6 cm×2.4 cm), and weight no more than 3 to 4 ounces (86 grams to 114 grams). In addition, meter 14 would be able to be easily operated by people having little manual dexterity and technical training.

In the preferred embodiment, clip 20 clips meter 14 to diaper 22. By contrast, meter 20 could be placed on a table or included in other equipment.

The temperature, time, and event data may be made at the person under test's home, or in a medical clinic, hospital, or nursing home. It is expected that the data will be analyzed by experienced personnel in lab and the results sent back to the person. The system and software could be purchased or rented with some instruction for analysis by a professional or for self analysis. The temperature vs. time data would be more secure and portable if the data logger had the ability to sort data on a ROM or RAM disk. Once the data were collected, a nurse could simply remove the disk and send it to a lab for analysis. Later the disk could be stored in the patient's medical file for future reference.

The undergarment may be a commercially available absorbent pad or diaper containing an embedded wire attached sensor 10 at one end and a plug in connector at the other end which attaches to meter 14 or pod 50. Tape or a velcro fastener may be used to hold the wire in place within the undergarment.

Figure 7:
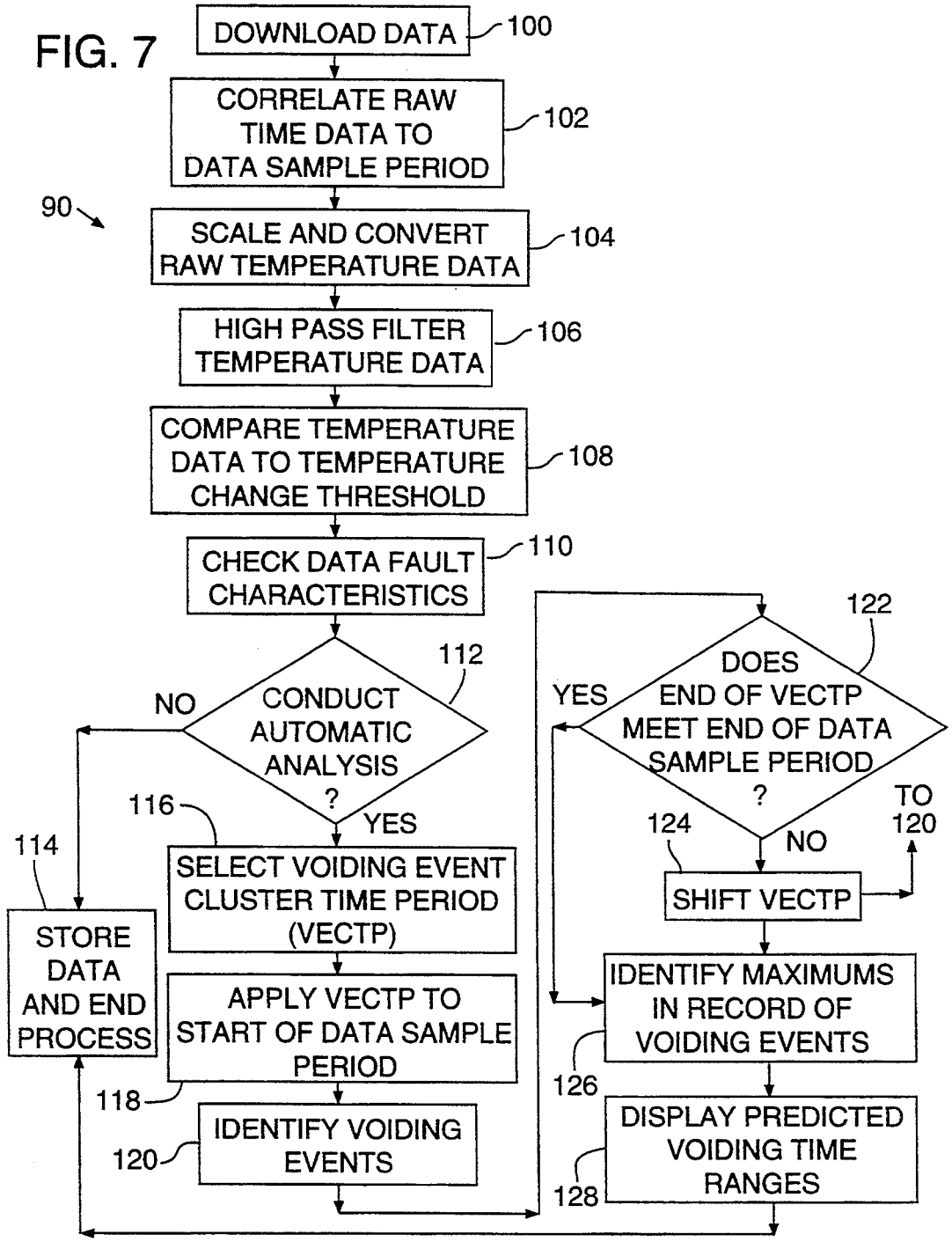
FIG. 7 is a flow diagram showing a preferred method of analyzing data obtained by the apparatus of FIG. 1.

FIG. 7 is a flow diagram showing a preferred process 90 by which computer 30 analyzes temperature and time data downloaded from meter 14 to predict time ranges during which future voiding events can be expected to occur. Operation of some aspects of process 90 are described with reference to FIG. 5. It will be appreciated, however, that references to FIG. 5 are merely for explanation and do not constitute all aspects of process 90.

Process block 100 indicates that raw time and temperature data are downloaded from meter 14 to computer 30, which is preferably a personal computer. The raw temperature data are in the form of digital electrical signals characteristic of sensor 10 and meter 14. Raw time data are represented by the intervals between the raw temperature data.

Process block 102 indicates that the raw time data are correlated with a predetermined data sample period, which is shown in FIG. 5 as being a 24-hour period but could be a period of any duration. The raw time data are correlated with the data sample period by aligning the beginning of the sequence of raw temperature data with the corresponding time in the data sample period. The beginning of the sequence of raw temperature data may be recorded, for example, by a manual notation of when meter 14 is activated.

Process block 104 indicates that the raw temperature data are linear scaled and converted into standard temperature units (e.g., Fahrenheit). While not necessary to the subsequent analysis of the temperature data for predicting future voiding events, this conversion provides temperature data of a form that facilitates review by an operator or care giver.

Linear scaled temperature data values $D_{in}$ of raw temperature data values $D'_{raw}$ are computed as:

$$D_{in} = D_{min} + D'_{raw}(D_{max} - D_{min}),$$

in which $D'_{raw}$ represent signal values ranging from zero to one and $D_{max}$ and $D_{min}$ are the respective maximum and minimum expected temperature data signal values to be generated by meter 14. The maximum and minimum expected temperature data signal values $D_{max}$ and $D_{min}$ correspond to respective temperatures of, for example, 50° F. and 105° F., which are selected according to typical temperature conditions of a person and the ambient environment.

The linear scaled temperature data values $D_{in}$ are converted to standard temperature units according to calculations specific to meter 14 and typically defined and promulgated by its manufacturer. With meter 14 implemented as, for example, a Rustrak Ranger with a sensor 12 in the form of a thermistor such as a skin thermistor having a temperature range of −50° C. through 100° C., manufactured by Yellow Springs, Inc. of Yellow Springs, Ohio, the linear scaled temperature data values $D_{in}$ are converted to standard temperature unit data (Celsius) $T(°C.)_{in}$ according to the following equation:

$$T(°C.)_{in} = (Y_A + Y_B(ln(D_{in})) + Y_C(ln(i\ D_{in}))^3)^{-1} - 273,$$

which is defined by the manufacturer of the specified meter 14 with the constants $Y_A$, $Y_B$, and $Y_C$ and their respective values 0.0014733, 0.0002372, and $1.074 \times 10^{-7}$ and the "ln" is the conventional notation for natural logarithm. The standard temperature unit data (Celsius) $T(°C.)_{in}$ may be converted to standard temperature unit data (Fahrenheit) $T(°F.)_{in}$ by the standard conversion:

$$T(°F.)_{in} = (9/5)T(°C.)_{in} + 32.$$

Process block 106 indicates that the standard temperature unit data $T(°F.)_{in}$ or $T(°C.)_{in}$ are high pass filtered to remove very low frequency ambient temperature changes and to emphasize relatively sudden variations corresponding to voiding events. Temperature variations occurring over periods greater than about 2 minutes (i.e., very low frequency temperature changes) can result from a variety of causes other than voiding, such as ambient temperature increases, movement of the person wearing the device, changes in the position of sensor 12, and removing the device. Such low frequency temperature changes can be relatively large (e.g., up to about 10° F.). In contrast, voiding events may be characterized and distinguished as higher frequency events. High pass filtering of the standard temperature unit data $T(°F.)_{in}$ or $T(°C.)_{in}$ is preferably performed by conventional differentiation of the data.

Process block 108 indicates that the filtered standard temperature unit data $T(°F.)_{in}$ or $T(°C.)_{in}$ are compared against a minimum temperature change threshold. Such a threshold comparison functions to distinguish voiding events from high frequency events with relatively low temperature changes, such as changes in body position. For example, increasing temperature changes of greater than 0.5° F. are be designated as corresponding to voiding events.

Process block 110 indicates that the filtered standard temperature unit data $T(°F.)_{in}$ or $T(°C.)_{in}$ are compared against a set of data fault characteristics to identify possible failures of meter 14 or sensor 12. Exemplary data fault characteristics are successive voiding events that are separated by less than a predetermined amount of time (e.g., 2 hours) and the absence of any voiding events over a predetermined period (e.g., 6 hours). Whenever a data fault characteristic is identified, an appropriate notice indication is made for the operator.

Inquiry block 112 indicates that an operator is queried as to whether automatic analysis of the voiding events should be conducted to predict time ranges for future voiding events. If so, inquiry block proceeds to process block 116. If not, inquiry block proceeds to process block 114.

Process block 114 indicates that data designated as corresponding to a voiding event in process block 108 are stored in nonvolatile memory for correlation with data from subsequent or prior readings taken by monitor 14 and process 90 is terminated.

Process block 116 indicates that a voiding event cluster time period is selected by the operator. As shown in FIG. 5, an exemplary voiding event cluster time period of one hour could be applicable to many circumstances. However, longer voiding event cluster time periods could be selected for analyzing relatively irregular voiding schedules and shorter voiding event cluster time periods could be selected for analyzing improved voiding control or scheduling.

Process block 118 indicates that the selected voiding event cluster time period is applied to the beginning of the data sample period comprising data acquired of multiple sampling periods. Referring to FIG. 5, for example, the selected voiding event cluster time period would be aligned with the one-hour period ending at 1:00 a.m.

Process block 120 indicates that the data designated as voiding events are scanned and counted to identify the number of voiding events during the selected voiding event cluster time period. The number of voiding events occurring within the selected voiding event cluster time period is recorded. Referring to FIG. 5, for example, the selected voiding event cluster time period aligned with the one-hour period ending at 1:00 a.m. would identify no voiding events.

Inquiry block 122 represents an inquiry as to whether the end of the selected voiding event cluster time period intersects the end of the data sample period. If not, inquiry block 122 proceeds to process block 124. If so, inquiry block 122 returns to process block 126.

Process block 124 indicates that the selected voiding event cluster time period is shifted by a preselected incremental interval (e.g., 5 minutes) within the data sample period. The size of the incremental interval is selectable by the operator to allow variation in data analysis resolution and speed. Referring to FIG. 5, for example, the selected voiding event cluster time period after the initial sampling would now be aligned with the one-hour period ending at 1:05 a.m. Process block 124 returns to process block 120.

Process block 126 indicates that the record of numbers of voiding events identified during the incrementally adjusted selected voiding event cluster time periods is reviewed to identify maximums in the values of recorded numbers, the maximums corresponding to clusters of voiding events. Typically, the maximums will extend over several successive selected voiding event cluster time periods and will correspond to a time range during which voiding events can be expected. It will be appreciated that decreasing the voiding event cluster time period could provide enhanced resolution in the determination of such time ranges.

Process block 128 indicates that computer 30 renders a display indicative of the time ranges during which voiding events can be expected. The display may be rendered graphically, as shown in FIG. 5, or as a text explanation. Process block 128 returns to process block 114.

Those skilled in the art will appreciate that many changes may be made in the above-described details of the preferred embodiment of the present invention without departing from the underlying principles thereof. The scope of the present invention should be determined, therefore, by the following claims.

I claim:

1. A method for accurately predicting approximate times a person without intervention would void, the person wearing an undergarment including a region that is near the urethral opening of the person, and a temperature sensor being positioned near the region, the method comprising the steps of:

sampling and measuring temperatures of the temperature sensor at times throughout a period to form temperature versus time data, the sampling and measurement being performed by a portable unit wearable by the person;

storing the temperature versus time data in the portable unit;

transferring the temperature versus time data to a computer;

analyzing the temperature versus time data with the computer to identify times of past voiding; and compiling the identified times of past voiding into clusters of multiple times of past voiding that fall within selected time ranges to predict time ranges during which the person would without intervention void.

2. The method of claim 1 in which the step of compiling includes determining a mean time of the identified times within the clusters.

3. The method of claim 1 in which analyzing the temperature versus time data includes filtering out temperature variations of less than a predetermined frequency.

4. The method of claim 3 in which filtering out temperature variations of less than a predetermined frequency includes differentiating the temperature versus time data.

5. The method of claim 1 in which times of past voiding are identified as increasing temperature changes of greater than a predetermined threshold amount.

6. The method of claim 1 further including comparing the temperature versus time data against a set of data fault characteristics to identify possible failures of the sensor or the portable unit.

7. The method of claim 1 in which compiling the identified times of past voiding into clusters includes scanning and counting the times of past voiding during successive voiding event cluster time periods to identify the number of voiding events during each successive voiding event cluster time periods and identifying the clusters as maxima in the numbers of times of past voiding.

8. The method of claim 7 in which the durations of the voiding event cluster time periods are selectable.

9. A method for predicting approximate times a person without intervention would void based on temperature versus time data acquired by a system having a temperature sensor positioned in a region that is near the urethral opening of the person, the method comprising:

processing the temperature versus time data to filter out temperature variations of less than a predetermined frequency;

identifying times of past voiding as increasing temperature changes of greater than a predetermined threshold amount; and compiling the identified times of past voiding into clusters of multiple times of past voiding that fall within selected time ranges to predict time ranges during which the person would without intervention void.

10. The method of claim 9 in which compiling the identified times of past voiding into clusters includes scanning and counting the times of past voiding during successive voiding event cluster time periods to identify the number of voiding events during each successive voiding event cluster time period and identifying the clusters as maxima in the numbers of times of past voiding.

11. The method of claim 10 in which the durations of the voiding event cluster time periods are selectable.

12. The method of claim 9 further including comparing the temperature versus time data against a set of data fault characteristics to identify possible failures of the sensor or the portable unit.

13. The method of claim 9 in which filtering out temperature variations of less than a predetermined frequency includes differentiating the temperature versus time data.

* * * * *